United States Patent [19]

Mapelli et al.

[11] Patent Number: 5,409,711
[45] Date of Patent: Apr. 25, 1995

[54] PHARMACEUTICAL FORMULATIONS

[75] Inventors: Luigi Mapelli; Marco G. R. Marconi, both of Milan; Marco Zema, Como, all of Italy

[73] Assignee: Eurand International SpA, Milan, Italy

[21] Appl. No.: 776,329

[22] PCT Filed: Apr. 9, 1991

[86] PCT No.: PCT/EP91/00689
 § 371 Date: Dec. 11, 1991
 § 102(e) Date: Dec. 11, 1991

[87] PCT Pub. No.: WO91/16043
 PCT Pub. Date: Oct. 31, 1991

[30] Foreign Application Priority Data

Apr. 17, 1990 [IT] Italy ..................... 20055/90

[51] Int. Cl.$^6$ .................... A61K 9/20; A61K 9/54; A61K 9/56
[52] U.S. Cl. ................... 424/490; 424/458; 424/461; 424/462; 424/464; 424/465; 424/468; 424/494; 424/496; 424/497; 514/772.3; 514/784; 514/785; 514/951; 514/970; 514/974
[58] Field of Search ............... 424/490, 497, 489, 465, 424/441, 458, 461, 462, 494

[56] References Cited

U.S. PATENT DOCUMENTS

| 4,675,175 | 6/1987 | Autant et al. ............ 424/233 |
| 4,762,702 | 8/1988 | Gergely et al. ............ 424/44 |
| 4,894,240 | 1/1990 | Geoghegan et al. ........ 424/497 |
| 5,051,262 | 9/1991 | Panoz et al. ............ 424/489 |

FOREIGN PATENT DOCUMENTS

| 0076515 | 4/1983 | European Pat. Off. . |
| 0077264 | 4/1983 | European Pat. Off. . |
| 0181564 | 5/1986 | European Pat. Off. . |

OTHER PUBLICATIONS

4 Page Rohm Pharma Technical Data Sheet dated Sep. 1982 entitled "Rapidly disintegrating, taste masking coatings with EUDRACIT ™ L 30 D produced in an Immersion Sword System".

Primary Examiner—Thurman K. Page
Assistant Examiner—James M. Spear

[57] ABSTRACT

The taste of orally administered drugs is masked by coating the drug with a polymeric membrane which is soluble only at a pH of 5 or more. An acid substance is included in the formulation containing the coated drug to reduce or prevent the dissolution of the membrane in the oral cavity.

10 Claims, No Drawings

PHARMACEUTICAL FORMULATIONS

This invention relates to pharmaceutical formulations, particularly formulations in which the taste of orally administered drugs is masked, to the preparation of such formulations and to a method for masking the taste of orally administered drugs.

The oral administration of solid forms, for example tablets, often presents ingestion problems for the patient, especially in the case of children or old people. In order to get around this problem other forms of pharmaceutical formulations are resorted to, for example chewable tablets, tablets which disgregate rapidly in the mouth or in a spoonful of water and monodose sachets, the contents of which are dissolved or suspended in a glass of water.

Unfortunately however many drugs have an unpleasant, bitter or irritating taste and therefore it is necessary to mask the taste. In order to mask the taste, particles of the drug may be coated with a membrane which prevents the release of the drug in water (if taken with water before ingestion) and in the oropharyngeal cavity during ingestion but liberates the drug after ingestion.

The most suitable membranes for this purpose are impermeable to water and saliva but dissolve as a function of the gastrointestinal pH. Among the most common membranes are those constituted by polymers which are insoluble in water or in acid environments but are soluble at pH greater than 5 as found in the intestine. However the pH of saliva is also greater than this value and so the partial dissolution of the membrane with consequent release of the unpleasant taste of the drug can begin in the oropharyngeal cavity.

It has now been found that this difficulty can be avoided or minimized by adding acidic substances to the orally administered pharmaceutical forms such that the acidic substances dissolve to create a microenvironment around the coated particles, which prevents the dissolution of the polymers making up the membrane. Thus the taste masking is maintained in the oral cavity by the coating on the drug.

Accordingly the present invention provides a pharmaceutical formulation for oral administration comprising a core comprising a drug, said core being coated with a polymeric membrane which is soluble only at a pH of 5 or greater and an acidic compound for reducing or preventing the dissolution of the membrane in the oral cavity.

The core may, for example, be the drug itself eg in crystalline form or it may be a granulate containing the drug.

The formulation may be prepared by coating the core with a polymer which forms the polymeric membrane and adding the acidic compound to the formulation.

The invention also provides a method for masking the taste of drugs contained in pharmaceutical formulations, in which the taste of the drug is masked by coating with a polymeric membrane which is soluble only at a pH of 5 or greater characterised in that an acidic compound is added to the formulation in order to reduce or prevent the dissolution of the membrane in the environment of the oral cavity.

According to the invention the drug will be released only when the coated cores (ie particles) have passed through the stomach and reached the intestine where there is a pH equal to or greater than 5 (this occurs rapidly especially if the stomach is empty, and when dealing with particles of small dimensions).

Another proposal suggests that a taste masking action may be obtained with a membrane which is insoluble at a high pH (greater than 5) and soluble at a low pH (1.2–1.5) such as for example Eudragit E; this would be insoluble in the oral cavity (thus having a favourable effect on masking the taste) and soluble in the gastric tract. However if the passage of the product is particularly rapid, as can happen with particles of small dimensions and on an empty stomach, there is a risk of having an incomplete dissolution of the membrane and so an incomplete absorption of the drug.

The present invention also differs from that described in patent EP-A-0101418 where substances, e.g. carbohydrates and polysaccharides, are added to formulations containing drugs coated with, for example, semipermeable and pH independent membranes. These substances prevent or slow down the release of the drug across the membrane, whereas in the present invention, the acidic compounds prevent the dissolution of the membrane coating on the drug rather than the dissolution of the drug.

The invention is particularly suitable for drugs having a particularly unpleasant taste or which are irritating to the oral cavity; cited as illustrative, but not limiting examples, of these drugs are ibuprofen, sodium diclofenac, acetylsalicylic acid, paracetamol, cimetidine, carboxymethylcysteine, Thiopronine, dextromethorphan hydrobromide, codeine and its salts, buflomedil, morphine and its salts, 5-aminosalicylic acid, macrolids and antibiotics such as penicillin and derivatives, erythromycin and its esters and ethers (eg roxithromycin), cephalosporins and tetracyclines.

Before coating it is convenient to granulate the drug although granulation is not essential.

The granulation is however useful for optimizing the granulometric distribution of the particles and may be carried out by using known dry (compacting) or wet techniques.

Preferably the core (eg comprising the drug in crystalline or granular form) has a size range of from 50, 100 or 200 μm to 1500, 1200 or 700 μm. Preferred size ranges are 100 to 1200 μm, particularly 200–700 μm.

In order to mask the unpleasant taste of the drug, this is coated with a membrane comprising polymers having a pH dependent solubility and more particularly polymers insoluble in an acidic environment and soluble at pH 5 or higher.

As illustrative but not limiting examples of these poloymers are cited: copolymers of methacrylic acid and methacrylic acid methyl ester (eg Eudragit L, Eudragit S), and copolymers of methacrylic acid ethyl ester (eg Eudragit L30D and L100-55), cellulose acetate phthalate, hydroxypropylmethylcellulose phthalate, polyvinyl acetate phthalate, shellac, hydroxypropylmethylcellulose acetate succinate, carboxymethylcelluose, cellulose acetate trimellitate or a copolymer of maleic acid and phthalic acid derivatives.

The coating of the drug with these polymers may be carried out by known procedures such as the following:
individual stages or a combination thereof as exemplified in U.S. Pat. Nos. 3,415,758 and 3,341,416 and in European Patent 0038585.
coating in coating pans as exemplified in Italian patent 929112 and in Canadian patent 879042
fluid bed coating as exemplified in U.S. Pat. Nos. 3,196,827 and 3,253,944 of D. E. Wurster.

The coated drug granules are very fine and irregular and therefore have a large surface area. Consequently the membrane is only a few micrometers thick, even when the percentage weight of the membrane is high, and thus in the brief time in which all or some of the particles remain, wholly or partially in the oral cavity, a dissolution or swelling, even partial, of the membrane can occur with consequent liberation of the unpleasant taste.

It has now been found that this difficulty can be avoided or minimized according to the present invention if an acidic substance is added to the formulation in a quantity such as to maintain a microenvironment at a pH of less than 5 during the transit stage in the oropharyngeal cavity. Obviously the more acidic the microenvironment the better it is, although an excess of acid can itself give an unpleasant flavour.

It has been found that the optimum quantity of acid varies as a function of the weight of the final pharmaceutical formulation. Preferably 1% to 20% by weight of acid compound is used. As illustrative but not limiting examples of acid compounds the following are cited: fumaric acid, citric acid and tartaric acid.

Formulations of the invention may be in a pharmaceutical form which is easily taken by children, old people or patients with ingestion difficulty. Examples are tablet and monodose sachet formulations. Examples of tablets are those that can be chewed or dissolved in the mouth or disgregate rapidly (eg within one minute) in a little (spoonful) of water; the monodose sachets can be taken directly or suspended in a small quantity of water (eg 20-50 ml).

The following Examples illustrate the invention.

EXAMPLE 1

(A) Preparation of the Granulate

Place 2000 g roxithromycin in a laboratory mixer, mix with an aqueous solution composed of 257 g of polyethyleneglycol 6000 and 600 g purified water.

Granulate with a 600 μm mesh and dry the granulate at about 45° C. Utilize the fraction between 500 and 210 μm.

(B) Fluid Bed Coating of the Granulate

Place 360 g Eudragit L 100-55, 121 g 1N sodium hydroxide, 122.1 g talc, 36 g triethylcitrate, 57.8 g liquorice flavouring and 1910 g purified water in a stainless steel container equipped with stirrer.

Place 1500 g of granulate (A) in a Granu-Glatt fluid bed container equipped with a Wurster insert and spray 2250 g of the previously prepared suspension through the atomizer.

Dry the granules at about 50° C. and sieve through the 600 μm mesh.

The release of the coated granules is determined in artificial juices according to the method described in USP XXII (Paddle, 200 rpm).

| TIME | RELEASE RATE | |
| (Minutes) | pH 4.5 | pH 6 |
| --- | --- | --- |
| −15 | 12.3% | 42.5% |
| −60 | — | 80.6% |

(C) Preparation of the Tablets

Place 346.8 g microcrystalline cellulose, 66 g Kollidon CL, 18 g sodium saccharin, 90 g fumaric acid, 6 g sodium laurylsulphate, 12 g aerosil, 30 g strawberry flavour, 12 g magnesium stearate and 451.2 g granulate (B) in a cube mixer.

Mix for 20-25 minutes and compress.

A tablet of 172 mg contains 50 mg of roxithromycin.

The formulation of these tablets has been studied so that they disintegrate in less than 30 seconds in a spoonful of water or directly in the mouth. In order to conserve the masking of the taste, fumaric acid was added which maintains a microenvironment at a pH lower than that of the membrane solubility.

The protection obtained is satisfactory; in fact as one sees from the data reported in paragraph (B), the release at a relatively acid pH is low, thus the unpleasant taste of the drug is not noticeable.

The release is complete at a pH greater than 5 therefore the active ingredient will be liberated in the intestinal tract as soon as these pH values are reached, as the bioavailability tests have demonstrated.

EXAMPLE 2

(A) Preparation of the granulate

Place 1400 g ibuprofen in a laboratory mixer and mix with a solution composed of 210 g 95% ethyl alcohol and 37 g ethylcellulose.

Granulate with a 500 μm sieve and dry the granulate at about 45° C. Use the fraction comprised between 500 and 210 μm.

(B) Coating of the granulate by coacervation.

Form a solution of 1870 g purified water, 100 g cellulose acetate phthalate and 25.7 g sodium bicarbonate.

Prepare a solution containing 600 g sodium sulphate in 2800 g purified water. Put in a vessel the previously prepared cellulose acetate phthalate solution, 1500 g sodium sulphate solution and 600 g of granulate (A). Mix for about 5 minutes and add the remainder of the sodium sulphate solution.

Filter the microcapsule obtained and wash with water until the sodium sulphate is eliminated. Dry the microcapsules at about 50° C. for 3-4 hours and sieve through the 600 μm mesh.

The release of the coated granulate has been determined in artificial juices according to the method described in USP XXII (Paddle, 150 rpm).

| TIME | RELEASE RATE | |
| (Minutes) | pH 1.2 | pH 7.2 |
| --- | --- | --- |
| −15 | <1% | — |
| −30 | — | 90% |

(C) Preparation of the Tablets

Into a cube mixer place 60 g microcrystalline cellulose, 70 g Kollidon CL, 4 g aspartame, 50 g fumaric acid, 1 g aerosil, 56 g strawberry flavour, 4 g liquorice flavour, 8 g magnesium stearate, 480 g granulate (B) and 80 g corn starch granulated with 2% of PVP K 30.

Mix for 20-25 minutes and compress.

One tablet of 406.5 mg contains 200 mg of ibuprofen.

Analogously to Example 1 the formulation of the tablets was studied in order to obtain a rapid disintegration in the mouth or in a spoonful of water and the fumaric acid was added to maintain the microenvironment at an acid pH.

EXAMPLE 3

(A) Preparation of the Granulate

Place 2000 g erythromycin in a laboratory mixer and mix for about 20 minutes with 1380 g of an aqueous solution of 15% hydroxypropylmethylcellulose. Granulate through a 720 μm mesh and dry in an oven at about 40° C. for 15-20 hours.

Utilise the fraction included between 500 and 210 μm.

(B) Coating of the Granulate in Fluid Bed

Place 550 g of the granulate (A) (500-210 μm) in a UNI Glatt fluid bed container equipped with a Wurster insert and spray, through the atomizer, 7140 g of a solution having the following composition: 428.7 g hydroxypropylmethylcellulose phthalate, 21.3 g plasticizers, 1340 g ethyl alcohol, 5350 g methylene chloride.

Dry the granules at about 50° C. and sieve through a 600 μm mesh.

The release of the coated granules was determined in artificial juices according to the method described in USP XXII (Paddle, 100 rpm)

| TIME | RELEASE RATE | |
|---|---|---|
| (Minutes) | pH 1.2 | pH 6 |
| −5 | <1% | — |
| −15 | <1% | 94% |

(C) Preparation of the Monodose Sachets

In a cube mixer, place 2490 g sorbitol, 165 g of xanthan gum, 18 g PVP K30, 1.5 g sodium saccharin, 37.5 g citric acid, 112.5 g grapefruit flavour, 22.5 g talc, 0.4 g sodium docusate and 873 g Granulate (B).

Mix for 20-25 minutes and divide into sachets made of paper/aluminium/atoxic polyethylene and thermoseal.

One 2400 g monodose sachet contains 250 mg ethryomycin.

Analogously to the procedure in Examples 1 and 2, citric acid is added to the sachet formulation to maintain the acid pH and therefore the masking of the taste in the oropharyngeal cavity.

Analogous results for the maintenance of the taste masking are obtained by the addition of acids in the final formulation when replacing erthromycin with cephalosporin or penicillin and their derivatives.

We claim:

1. A pharmaceutical formulation for oral administration comprising a core consisting essentially of a drug, said core being coated with a polymeric membrane which is soluble only at a pH of 5 or greater and an acidic compound mixed with the coated core for reducing or preventing the dissolution of the membrane in the oral cavity.

2. A formulation as claimed in claim 1 wherein the acidic compound is fumaric acid, citric acid or tartaric acid or a mixture of one or more of said acids.

3. A formulation as claimed in claim 1 in which the acidic compound comprises 1 to 20% by weight of the pharmaceutical formulation.

4. A formulation as claimed in claim 1 in which the polymeric membrane comprises a polymer selected from the group consisting of a copolymer of methacrylic acid and methacrylic acid methyl ester or methacrylic acid ethyl ester, cellulose acetate phthalate, hydroxypropylmethylcellulose phthalate, polyvinyl acetate phthalate, shellac, hydroxypropylmethylcellulose acetate succinate, carboxymethylcellulose, cellulose acetate trimellitate or a copolymer of maleic acid and a derivative of phthalic acid.

5. A formulation as claimed in claim 1 in which the drug is selected from the group consisting of ibuprofen, sodium diclofenac, acetylsalicylic acid, paracetamol, cimetidine, carboxymethylcysteine, Thiopronine, dextromethorphan hydrobromide, codeine and its salts, buflomedil, morphine and its salts, 5-aminosalicylic acid, macrolids and antibiotics including penicillins, erythromycin and its esters and ethers, cephalosporins and tetracyclines.

6. A formulation as claimed in claim 1 in which the size of the core is within the range 100 to 1200 μm.

7. A formulation as claimed in claim 6 in which the size of the core is within the range 200 to 700 μm.

8. A formulation as claimed in claim 1 in the form of a tablet or sachet.

9. A process for preparing a pharmaceutical formulation as claimed in claim 1 which comprises coating the core with a polymer to form the polymeric membrane and adding the acidic compound to the formulation.

10. A method for masking the taste of drugs contained in pharmaceutical formulations in which the taste of drug is masked by coating a core consisting essentially of a drug with a polymeric membrane which is soluble only at a pH of 5 or more and mixing an acidic compound with the coated core in order to reduce or prevent the dissolution of the membrane in the environments of the oral cavity.

* * * * *